United States Patent [19]

Tytgat et al.

[11] 4,256,542

[45] Mar. 17, 1981

[54] PROCESS AND DEVICE FOR MONITORING THE CHANGE IN THE SURFACE CONDITION OF A METAL COMPONENT IN AN INSTALLATION CONTAINING AN IONIC PHASE

[75] Inventors: Daniel Tytgat, Brussels; Albert Degols, Berg; François Dujardin, Brussels, all of Belgium

[73] Assignee: Solvay & Cie, Brussels, Belgium

[21] Appl. No.: 34,680

[22] Filed: Apr. 30, 1979

[30] Foreign Application Priority Data

May 5, 1978 [FR] France .............................. 78 13602

[51] Int. Cl.$^3$ ...................... G01N 27/46; G01N 27/30
[52] U.S. Cl. .................................. 204/1 T; 204/195 C
[58] Field of Search ............ 204/1 C, 195 C; 324/29, 324/71 R

[56] References Cited

U.S. PATENT DOCUMENTS

| 3,716,460 | 2/1973 | Weisstuch et al. .................. 204/1 C |
| 4,155,814 | 5/1979 | Tejfalussy et al. .................. 204/1 C |

OTHER PUBLICATIONS

A. J. Diefenderfer, "Principles of Electronic Instrumentation", W. B. Saunders Co., 1972, pp. 309 and 552.

Primary Examiner—Aaron Weisstuch
Attorney, Agent, or Firm—Robert E. Burns; Emmanuel J. Lobato; Bruce L. Adams

[57] ABSTRACT

The invention relates to a process and a device for monitoring the change in the surface condition of a metal component in an installation containing an ionic phase, by a modification of the working conditions in the installation, relative to standard working conditions. The equilibrium potential of the component in the ionic phase in the installatoin is applied to one electrode of an electrochemical measuring cell, the electrode and the cell respectively reproducing the metal component and the installation under standard working conditions, and the intensity of the resulting electric current in the measuring cell is measured. The invention applies, in particular, to the monitoring of the corrosion of the wall of a steel pipeline through which a sodium chloride brine passes.

14 Claims, 3 Drawing Figures

PROCESS AND DEVICE FOR MONITORING THE CHANGE IN THE SURFACE CONDITION OF A METAL COMPONENT IN AN INSTALLATION CONTAINING AN IONIC PHASE

FIELD OF INVENTION

The object of the present invention is to monitor the change in the surface condition of a metal component in an installation containing an ionic phase.

It relates more particularly to a process and a device for monitoring the action exerted on the surface condition of such a component by at least one modification of the working conditions in the said installation.

BACKGROUND OF THE INVENTION

In general, phenomena affecting the surface condition of a metal component in an installation containing an ionic phase (for example an electrolytic liquid) can be influenced by various working conditions, amongst which there may be mentioned, in particular, the nature of the material constituting the component in question, the shape, the dimensions and the surface condition of the latter (in particular its roughness), the characteristics of the ionic phase treated in the installation (for example the value of the pH), the pressure or temperature conditions in the installation, the possible presence of a galvanic couple between two different metals or alloys, a local deterioration of a film for protecting a wall of the installation (for example a deterioration of the layer of zinc on a galvanized steel pipe), the appearance of a localized air pocket in a dead zone of the installation, the presence of an electrokinetic phenomenon in a constricted zone of piping in which the ionic phase circulates, the existence of anodic or cathodic protection for the installation, and the like. Furthermore, the phenomena affecting the surface condition of the metal component in the installation can be of a diverse nature and can consist, in particular, of corrosion, erosion or encrustation.

Thus, in the presence of hard water, there is generally a gradual scaling-up of the metal installations; this scaling-up, which is particularly significant in the case of hot water, leads to a gradual clogging of the installations and to a drop in the efficiency of the heat exchangers.

In the presence of chemically aggressive water, such as softened water, stainless steel or galvanized steel installations run the risk of suffering local corrosion which can sometimes lead to a hole in the wall of the installation.

If the liquids treated contain suspended solids, local erosion of the walls of the installation, or sedimentation in those zones of the installation in which the liquid undergoes a sudden pressure loss, such as the widenings in piping or the elbows, is sometimes observed.

Erosion or sedimentation phenomena can occur, in particular, in installations through which viscous liquids, such as sludges, pass, or in evaporator/crystallizers such as those commonly used for the treatment of aqueous solutions of caustic soda originating from cells for the electrolysis of sodium chloride brine.

In general, it is important to be able to determine with precision the influence that these various working conditions can exert, in isolation or in combination, on the change in the surface condition of a given metal component in an installation containing an ionic phase.

Furthermore, during the operation of an industrial installation, it is important to be able to monitor, at any time, the change in the surface condition of the metal components constituting the installation, so that the appearance of a serious anomaly in this surface condition can be detected rapidly and so that it is then possible to react immediately and alter the working conditions in the installation in order to rectify this anomaly.

It is known to use methods of gravimetric measurement for controlling the corrosive or encrusting nature of liquids circulating in installations (Materials Protection, October 1962, pages 10 to 19 and 27). These known methods consist in periodically extracting, from the liquid, a probe which is normally immersed therein, in scraping from the probe the materials which may have become encrusted thereon, and in weighing these materials and also the probe. A comparison of the weight of the probe before and after the test makes it possible to assess the corrosive nature of the liquid, whilst the weight of the materials which have become encrusted on the probe during the test is a measure of the encrusting nature of the liquid. These known methods exhibit the disadvantage of being slow and relatively imprecise, and they are incapable of providing an instantaneous indication of the surface condition of an installation in which the liquid is being treated.

It has also been proposed to monitor the corrosive nature of liquids circulating in metal installations by measuring the variation, with time, of the electrical resistance of a probe immersed in the liquid (Corrosion, National Association of Corrosion Engineers, Volume 14, March 1958, pages 155t to 158t). Although it permits precise monitoring of the aggressiveness of the liquid, this known process does not make it possible to evaluate the rate of degradation of the material constituting the installation.

In order to overcome this disadvantage, the technique referred to as the "slope at the origin" method (also known as the "polarization resistance" method) has been proposed; this technique consists in immersing, in the liquid, a probe made of an identical material to that of the installation examined, and in determining the current/voltage ration in the region of the equilibrium potential of the probe. This technique makes it possible to evaluate the change in the surface condition of the probe, but it involves the use of expensive precalibrated probes which should be replaced periodically. This known technique exhibits the additional disadvantage that it does not generally permit instantaneous and continuous measurements.

It has also been proposed to monitor the formation of deposits or encrustations on a wall in contact with a liquid, for example the wall of a heat exchanger, by measuring the variation, with time, of the temperature of the wall by means of a thermocouple housed in the wall (Chemical Engineering Progress July 1975, Volume 71, No. 7, pages 66 to 72). However, this known method is not suitable for monitoring the corrosive nature of the liquid. It also exhibits the disadvantage of being highly dependent on the temperature variations in the medium in contact with the wall.

U.S. Pat. No. 3,612,998 proposes a process for detecting corrosion caused by an electrokinetic phenomenon created by the travel of a liquid at high speed in the vicinity of a metal component, the process consisting in measuring the electric current generated by the continuous dissolution of the metal component in the liquid, under the effect of the electrokinetic phenomenon.

This known process exhibits the disadvantage that it only applies to a particular type of corrosion, namely that caused by the flow of liquids at very high speed. It is not capable of detecting other types of corrosion, such as, for example, that which is inherent in the aggressiveness of soft waters, or of detecting erosion or encrustation. It exhibits the additional disadvantage that it does not represent the surface condition of the metal component and, consequently, it does not make it possible to assess the type of corrosion suffered by the metal component.

The known processes described above all exhibit the additional disadvantage that they are incapable of detecting the cause which gives rise to the appearance of a phenomenon affecting the surface condition of a metal component in the installation. In other words, although they detect, generally with precision, the appearance of such a phenomenon, for example local corrosion, these known processes provide no indication as regards the inadvertent modifications which have occurred in the working conditions of the installation and which give rise to the appearance of this phenomenon. Similarly, these known processes do not make it possible to easily assess the influence which a given modification of the working conditions would exert on the surface condition of the metal components in the installation.

SUMMARY OF THE INVENTION

The Applicant has now found a process which makes it possible to avoid the disadvantages and the abovementioned inadequacies of the known processes.

Consequently, the invention relates to a process for monitoring the action exerted on the change in the surface condition of a metal component in an installation containing an ionic phase, by at least one modification of the working conditions in the said installation, relative to standard working conditions, according to which process the equilibrium potential of the component in the ionic phase in the installation of which the working conditions are affected by the abovementioned modification, is applied to one electrode of at least one electrochemical measuring cell, the electrode and the cell respectively reproducing the component and the installation under the standard working conditions, and the intensity of the resulting electric current in the cell is measured.

Within the scope of the invention, the term "metal component" is intended to denote any solid or liquid component which, under the working conditions of the installation, is an electronic conductor of electricity. In general, a component of this kind can be chosen not only from amongst all the metals and alloys, but also from amongst other substances such as, in particular, carbon and graphite. By way of example, the metal component can consist of a metal wall, a solid metal member (such as a flap, a valve, a rotor vane of a pump, a gear pinion, a baffle in pipelines, and the like), a graphite crucible, or a liquid such as a liquid metal, for example a bed of mercury.

The term "ionic phase" is understood as denoting a solid, liquid or gas phase which, under the working conditions of the installation, is an ionic conductor of electricity.

In the case where the ionic phase is a liquid, the latter can be, for example, a pure liquid, a mixture of liquids, a solution or an electrolytic suspension, such as water, an aqueous solution of an alkali metal chloride or calcium chloride and/or or of an alkali metal hydroxide or calcium hydroxide, a sludge, crude petroleum and the like.

The term "standard working conditions" denotes a set of known conditions which are predetermined and maintained invariable.

Within the scope of the invention, the term "modification of the workingconditions" is understood as denoting, at one and the same time, a variation in the magnitude of a parameter governing the operation of the installation, relative to a standard value (for example a variation in the temperature or pressure of the ionic phase, a variation in its composition, a variation in the temperature of the metal component in the installation which is in contact with the ionic phase, a variation in the equilibrium potential of the metal component, and the like), the imposition of an additional working condition, relative to the standard conditions (for example the incorporation of a corrosion inhibitor in the case where the ionic phase is a liquid, the imposition of anodic or cathodic protection, the incorporation of an additional member, such as a stirrer, into the installation, the appearance of a galvanic couple between the metal component in question and another metal component in the installation, and the like), or the elimination of one or more of the standard working conditions.

In the process according to the invention, the magnitude of the resulting current in the electrochemical measuring cell in a measure of the rate at which the surface condition of the metal component changes under the effect of the modification envisaged, relative to the standard working conditions (for example the rate of corrosion and/or erosion of the surface of the metal component).

In a particular embodiment of the process according to the invention, the abovementioned potential is applied to several electrodes respectively belonging to several different electrochemical measuring cells in which different standard working conditions prevail.

This particular embodiment of the invention makes it possible simultaneously to monitor the influence separately exerted by several different modifications of the working conditions, taken in isolation or in combination, on the change in the surface condition of the metal component in the installation.

In order to carry out the process according to the invention, a monitoring device can be used which, according to the invention, comprises:

a control electrochemical measuring cell, comprising an electrode and an ionic phase which respectively reproduce the metal component and the ionic phase in the installation of which the working conditions are affected by the abovementioned modification;

a comparison cell comprising an electrode and an ionic phase which respectively reproduce the metal component and the ionic phase in the installation under standard working conditions;

a potentiostatic circuit which connects the two cells to one another and is driven by the control cell; and a member for measuring the intensity of the resulting electric current in the comparison cell.

In general, the term potentiostatic circuit is understood as meaning an electronic circuit which is designed to keep the potential of an electrode, which is in contact with an ionic phase, equal to that of a command signal, regardless of the effects of electrical or electrochemical origin to which the electrodes are subjected.

In a preferred embodiment of the device according to the invention, the control cell, its electrode and its ionic phase consist respectively of the installation, the metal component in question, in the installation, and the ionic phase of the installation.

This particular embodiment of the device according to the invention has the advantage that it simplifies the construction of the control cell.

The process and the device according to the invention exhibit the advantageous characteristic that they rapidly detect the appearance of an anomaly in the working conditions of an installation containing an ionic phase, and also the repercussions which this anomaly can have on the surface condition of the metal component in the installation.

As a variant, the process and the device according to the invention can also be used to predict the effect which could be exerted, by a particular modification of the working conditions in the installation, on the surface condition of the metal component in an installation containing an ionic phase.

The invention can be applied to the monitoring of the change in the surface condition of any solid or liquid metal component in an installation in which this component is in contact with an ionic phase. In particular, the invention finds a valuable application in the monitoring of the corrosion, erosion and encrustation phenomena affecting the walls of metal pipelines for conveying liquids (for example of pipes for conveying brine), heat exchangers in which corrosive, abrasive or encrusting liquids are treated (for example cooling towers or evaporators, such as evaporators used for concentrating alkaline brines obtained by the electrolysis of sodium chloride brines in cells with a permeable diaphragm), the walls and the plates of carbonation columns in soda factories using the ammonia process, and the like.

BRIEF DESCRIPTION OF DRAWINGS

Characteristics and details of the invention will become apparent from the following description of the attached figures, which are given solely by way of examples.

In these figures identical components are denoted by the same reference numbers.

DESCRIPTION OF PREFERRED EMBODIMENTS

Figure 1:
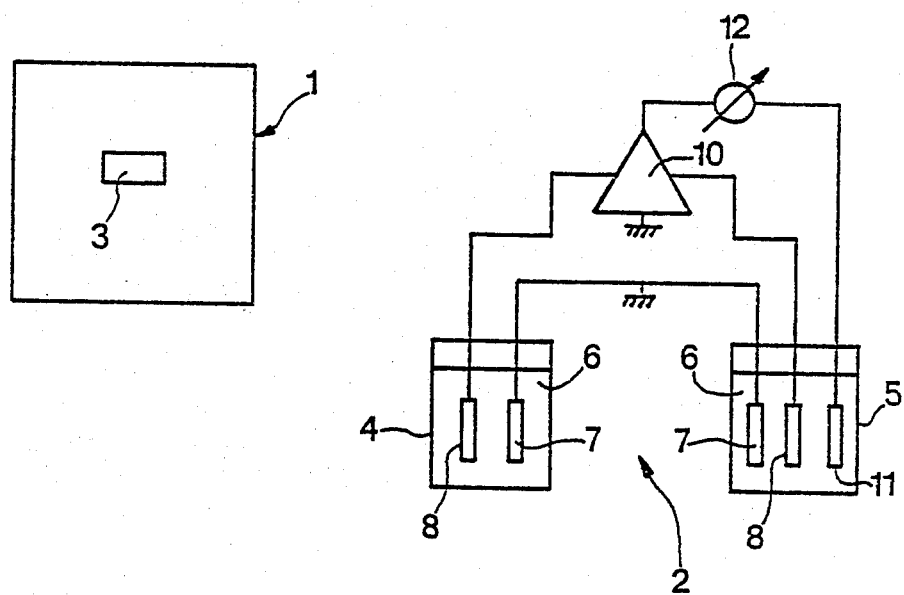
FIG. 1 is a diagram of an embodiment of the device according to the invention.

FIG. 1 schematically represents, at 1, on a small scale, an installation containing an ionic liquid and, at 2, on a large scale, a particular embodiment of the device according to the invention. This device is designed to monitior the change in the surface condition of a metal component 3 in the installation 1, due to the effect of a modification of the working conditions of the installation 1 relative to standard conditions.

According to the invention, the device 2 comprises two electrochemical measuring cells 4 and 5, each of which contains an electrolyte 6 in which are immersed a test or work electrode 7 and a reference electrode 8, for example an electrode containing calomel saturated with KCl.

The cell 4 is a control cell for the installation 1. For this purpose, its work electrode 7 represents the metal component 3 in the installation (the electrode is made, for example, of the same metal or alloy as the component 3 and it optionally possesses the same profile and the same roughness as this component); its enclosure 4a may represent the walls of the installation 1, which are located in the vicinity of the component 3 and may form a galvanic couple with this component, and its electrolyte 6 is identical to the liquid treated in the installation 1. Furthermore, the same instantaneous ambient conditions prevail in the control cell 4 as in the installation 1 (for example, the same temperature, the same pressure, the same flow rate of the liquid, and the like).

The cell 5 is a comparison cell. Predetermined standard working conditions prevail therein. For example, the two cells 4 and 5, and their work elctrodes 7, are identical, but the electrolyte 6 of the cell 5 differs from that of the cell 4 in the value of the pH.

The reference electrodes 8 of the two cells 4 and 5 are respectively connected to the non-inverting and inverting terminals of a potentiostat 10 which is connected to an auxiliary electrode 11 immersed in the electrolyte 6 of the comparison cell 5. The two work electrodes 7 are connected to the earth or ground terminal of the potentiostat 10. The potentiostat 10 acts so that the potential of the electrode 7 of the cell 5 is constantly equal to the equilibrium potential of the electrode 7 of the cell 4. The electrical current which results therefrom is measured by an ammeter 12 which is connected in series in the circuit of the auxiliary electrode 11. The magnitude of this electrical current is a measure of the change undergone by the surface condition of the component 3 in the installation 1, due to the effect of the modifications of the working conditions in the installation 1, relative to the standard working conditions prevailing in the cell 4. This change in the surface condition of the component 3 can consist, for example, of an increase in the corrosion, erosion or encrustation which appears on its surface.

Figure 2:
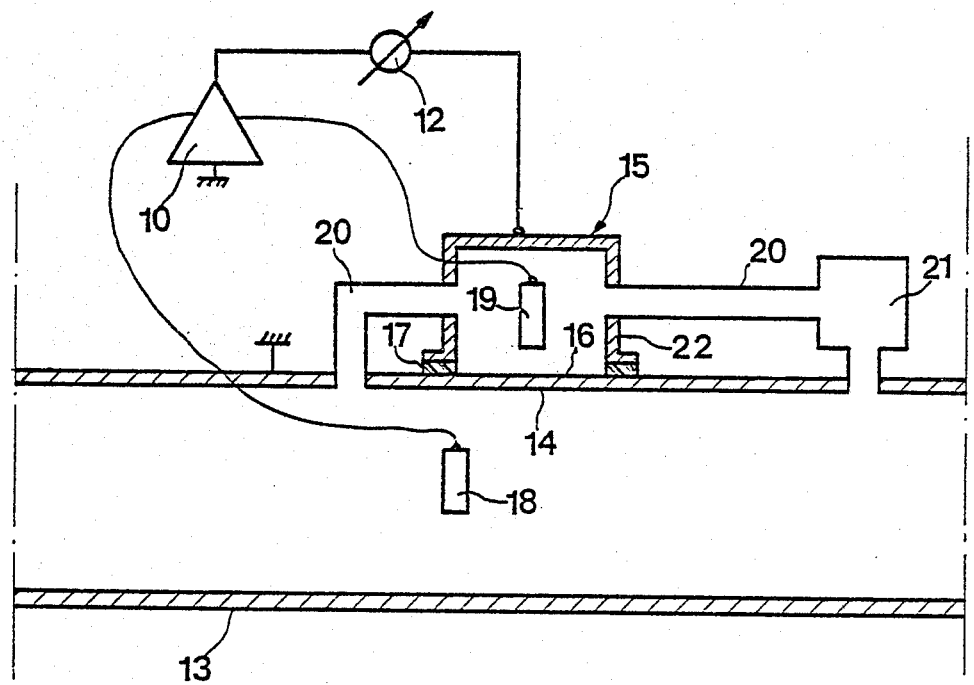
FIG. 2 is a diagram of another particular embodiment of the device according to the invention.

FIG. 2 schematically shows a particular embodiment of the device according to the invention, which device is applied to the monitoring of the surface condition of the metal wall of a pipeline 13 through which a liquid passes.

By way of example, in the particular case considered, a saturated sodium chloride brine passes through the pipeline 13, which is made of steel.

In the case of the installation of FIG. 2, the object of the method according to the invention consists in continuously monitoring whether or not the wall of the pipeline is the subject of local corrosion due to the accidental presence of oxygen in the brine. For this purpose, according to the embodiment shown in FIG. 2, the monitoring device according to the invention comprises a control cell formed by the actual pipeline 13; the work electrode of this control cell consists of the inner face 14 of the wall of the pipeline 13. The comparison cell of the device is formed by an annular enclosure 15 which is fixed against the outer face 16 of the wall of the pipeline 13, with the interposition of a gasket 17 made of a material which does not conduct electricity. The work electrode of the comparison cell consists of the outer face 16 of the wall of the pipeline 13.

Two identical reference electrodes 18 and 19, for example, electrodes containing calomel saturated with KCl, are respectively housed in the pipeline 13, in the region of its wall, and in the enclosure 15, in the region of its work electrode 16. The two reference electrodes 18 and 19 are respectively connected to non-inverting and inverting input terminals of a potentiostat 10 which is connected to an auxiliary electrode consisting of the peripheral wall 22 of the enclosure 15, which wall is made, for this purpose, of a metal which is inert with respect to brine. Furthermore, the pipeline 13 is connected to the earth or ground terminal of the potentiostat 10.

Brine, originating from the pipeline 13, passes through the enclosure 15 via a branch 20 comprising a chamber 21 in which the branched-off fraction of brine is deaerated by bubbling an inert gas through it. The flow rate of brine in the enclosure 15 is adjusted so as to ensure that the flow rate, in the enclosure, along the electrode 16 is equal to that existing along the electrode 14.

The potentiostat 10 keeps the potential of the electrode 16, relative to the reference electrode 19, constantly equal to the equilibrium potential of the electrode 14 in the brine circulating in contact therewith in the pipeline 13.

As long as the brine circulating in contact with the electrode 14 in the pipeline 13 does not contain oxygen, the working conditions in the pipeline 13 and in the enclosure 15 are identical, with the result that the ammeter 12 indicates a zero current.

If the brine circulating in the pipe 13 accidentally contains a small amount of oxygen, the working conditions in the pipeline 13 become different from the standard conditions prevailing in the enclosure 15, because the brine which is introduced into the pipeline via the pipe 20 has been deaerated beforehand in the chamber 21. The result is the immediate appearance of an electric current indicated by the ammeter 12. The appearance of this electric current is an indication of the appearance of a modification in the working conditions prevailing in the pipeline 13, relative to the standard conditions (this modification consisting of the accidental appearance of oxygen in the brine); furthermore, provided the area of the electrode 16 is known, the magnitude of this electric current is a measure of the rate of the corrosion suffered by the face 14 of the wall of the pipeline.

The experiments which now follow will show the value of the invention.

In each of these experiments, the influence of the presence of ferric ions, in a molar aqueous solution of hydrochloric acid, on the rate of dissolution of mild steel was studied by means of the device 2 of FIG. 1. For this purpose, the electrolyte 6 of the control cell 4 consisted of a molar aqueous solution of hydrochloric acid, containing 100 ppm of the product known under the name Dehyquart (Henkel GmbH), which is an alkylpyridinium-based corrosion inhibitor, and also a defined amount of ferric ions which were added in the form of ferric chloride.

The electrolyte 6 of the comparison cell 5 consisted of a molar aqueous solution of hydrochloric acid, which had the same concentration of Dehyquart corrosion inhibitor as in the cell 4, but which was free from ferric ions.

The temperature and the stirring of the electrolytes 6 were identical in the two cells 4 and 5 and the working pressure therein was atmospheric pressure.

The work electrodes 7 of the two cells consisted of cylindrical bars of mild steel; the bar 7 of the comparison cell 5 had a total area of 10 $cm^2$.

Electrodes containing calomel saturated with KCl were used as the reference electrodes 8, and the auxiliary electrode 11 consisted of a platinum wire.

Five consecutive experiments were carried out, corresponding to respective proportions of 10 mg/liter, 30 mg/liter, 100 mg/liter, 300 mg/liter and 1,000 mg/liter of ferric ions in the hydrochloric acid in the control cell 4. During each experiment, which lasted about 7 to 8 minutes, the value of the current density, expressed in $\mu A$ per $cm^2$ of area of the electrode 7 of the comparison cell 5, was read off from the ammeter 12, and the corresponding rate of corrosion of the electrode (expressed as mm of thickness per year) was calculated.

Figure 3:
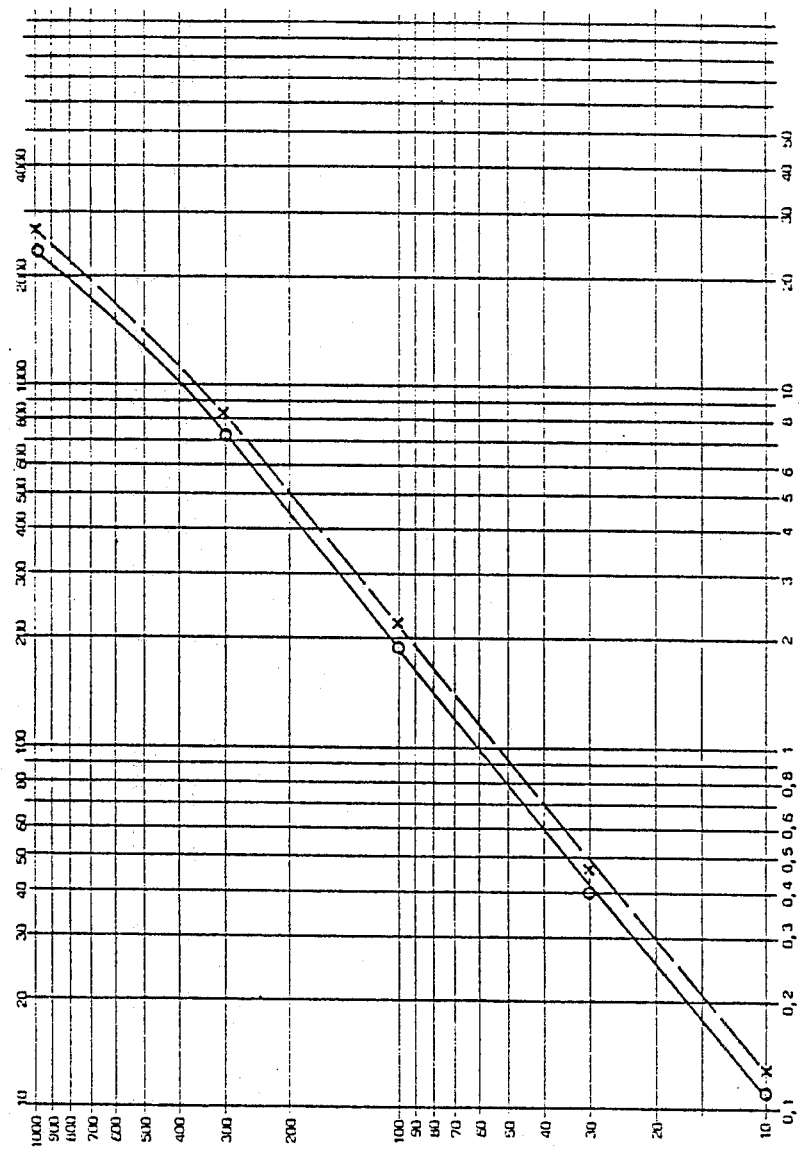
FIG. 3 is a graph plotted on the basis of the results of experiments carried out with the device of FIG. 1.

The results of the five experiments have been plotted on the graph of FIG. 3. In this graph, the scale of the ordinate expresses the concentration, in mg/litre, of ferric ions in the hydrochloric acid in the control cell 4, the upper scale of the abscissa expresses the current density, in $\mu A/cm^2$, and the lower scale of the abscissae expresses the corresponding rate of corrosion, in mm/year, of the mild steel. The continuous curve represents the change in the current density as a function of the proportion of ferric ions, and the broken curve represents the change in the corrosion of the mild steel as a function of the proportion of ferric ions.

The invention is not limited to the above description, it being possible for numerous modifications to be applied thereto.

I claim:

1. Process for monitoring or predicting a change in the surface condition of a metal component in contact with an ionic phase in an installation which comprises:
   providing a control cell comprising a work electrode of the same metal as said meta component, a reference electrode and an electrolyte reproducing said ionic phase of said installation, actual working conditions prevailing in said control cell,
   providing a comparison cell comprising a work electrode, a reference electrode and an electrolyte and maintaining standard working conditions in said comparison cell,
   applying the equilibrium voltage of said control cell, to said comparison cell so as to oppose the voltage of said comparison cell and measuring the resultant current, if any, through said comparison cell.

2. Process according to claim 1, in which said equilibrium voltage of said control cell is continuously measured and continuously applied to said comparison cell, and the resultant current is continuously monitored.

3. Process according to claim 2, in which said comparison cell further includes an auxiliary electrode, and in which said control cell and said comparison cell are connected by connecting lines to a potentiostat and said resultant current is measured by an ammeter in a line connecting said auxiliary electrode of said comparison cell with said potentiostat.

4. Process according to claim 1, in which said metal component comprises said work electrode of said control cell.

5. Process according to claim 4, in which said change in the surface condition of said metal component is corrosion.

6. Process according to claim 4, in which said change in the surface condition of said metal component is incrustation.

7. Process according to claim 1, in which said metal component comprises an enclosure wall of said installation and comprises said work electrodes of said control cell and of said comparison cell.

8. Process according to claim 7, in which one surface of said wall comprises said work electrode of said control cell and another surface of said wall comprises said work electrode of said comparison cell.

9. Apparatus for monitoring or predicting a change in the surface condition of a metal component in contact with an ionic phase in an installation, comprising:
- a control cell comprising a work electrode of the same metal as said metal component, a reference electrode and an electrolyte reproducing said ionic phase of said installation, under actual working conditions,
- a comparison cell comprising a work electrode, a reference electrode and an electrolyte under standard working conditions,
- means for applying the equilibrium voltage of said control cell to said comparison cell so as to oppose the voltage of said comparison cell, and means for measuring the resultant current, if any, through said comparison cell.

10. Apparatus according to claim 9, in which said comparison cell further includes an auxiliary electrode, and in which said means for applying the equilibrium voltage of said control cell to said comparison cell comprises a potentiostat to which said cells are connected, and said means for measuring the resultant current, if any, through said comparison cell comprises an ammeter in a connection between said auxiliary electrode of said comparison cell and said potentiostat.

11. Apparatus according to claim 9, in which said metal component comprises said work electrode of said control cell.

12. Apparatus according to claim 9, in which said installation comprises an enclosure having a metal wall which comprises said work electrode of said control cell.

13. Apparatus according to claim 9, in which said installation comprises an enclosure having a metal wall one surface of which comprises said work electrode of said control cell and another surface of which comprises said work electrode of said comparison cell.

14. Apparatus according to claim 9, in which each of said reference electrodes of said cells is an electrode containing calomel saturated with KCl.

* * * * *